(12) United States Patent
Steger et al.

(10) Patent No.: US 11,253,638 B2
(45) Date of Patent: Feb. 22, 2022

(54) MONITORING DEVICE AND METHOD FOR MONITORING AN EXTRACORPOREAL BLOOD TREATMENT DEVICE

(71) Applicant: B. BRAUN AVITUM AG, Melsungen (DE)

(72) Inventors: Jennifer Steger, Wurmlingen (DE); Peter Bruchhäuser, Kassel (DE); Günter Nissen, Melsungen (DE)

(73) Assignee: B. BRAUN AVITUM AG, Melsungen (DE)

(*) Notice: Subject to any disclaimer, the term of this patent is extended or adjusted under 35 U.S.C. 154(b) by 402 days.

(21) Appl. No.: 16/261,873

(22) Filed: Jan. 30, 2019

(65) Prior Publication Data

US 2019/0231963 A1   Aug. 1, 2019

(30) Foreign Application Priority Data

Jan. 31, 2018   (DE) .......................... 102018102171.2

(51) Int. Cl.
*A61M 1/36* (2006.01)
*A61M 1/16* (2006.01)

(52) U.S. Cl.
CPC ............ *A61M 1/3656* (2014.02); *A61M 1/16* (2013.01); *A61M 1/1601* (2014.02);
(Continued)

(58) Field of Classification Search
CPC .... A61M 1/16; A61M 1/1601; A61M 1/1605; A61M 1/1607; A61M 1/1623;
(Continued)

(56) References Cited

U.S. PATENT DOCUMENTS 8,617,093 B2   12/2013   Kopperschmidt et al.
9,801,994 B2   10/2017   Ritter et al.
(Continued)

FOREIGN PATENT DOCUMENTS

DE   102009024864 A1   12/2010
DE   102009060668 A1   6/2011
(Continued)

OTHER PUBLICATIONS

German Search Report for German Application No. 10 2018 102 171.2, dated Jan. 1, 2019, with translation, 12 pages.
(Continued)

*Primary Examiner* — Nicholas J. Weiss
*Assistant Examiner* — Seth Han (57) ABSTRACT

A device and method are used for monitoring an extracorporeal blood treatment device, such as a dialysis machine, which includes an extracorporeal blood circuit having an arterial blood line with an arterial patient port and/or at least one venous blood line with a venous patient port, and a dialysis fluid system which has a dialysis fluid supply line and a dialysis fluid drain line. The monitoring device selects and senses a measured value during operation of the extracorporeal blood treatment device which is suitable for monitoring the blood treatment device to compare a time-related actual course of the measured value with a target course of the measured value stored in a memory, and to determine that there is a defect if, at least in sections, the actual course of the measured value deviates from the target course by more than a defined tolerance.

12 Claims, 4 Drawing Sheets

(52) U.S. Cl.
CPC ........ *A61M 1/3639* (2013.01); *A61M 1/3655* (2013.01); *A61M 1/3661* (2014.02); *A61M 1/1605* (2014.02); *A61M 1/1607* (2014.02); *A61M 1/1623* (2014.02); *A61M 1/1631* (2014.02); *A61M 1/1647* (2014.02); *A61M 1/3663* (2013.01); *A61M 2205/18* (2013.01); *A61M 2205/3317* (2013.01); *A61M 2205/3327* (2013.01); *A61M 2205/3334* (2013.01); *A61M 2205/3365* (2013.01); *A61M 2205/3368* (2013.01); *A61M 2205/52* (2013.01); *A61M 2205/581* (2013.01); *A61M 2205/582* (2013.01); *A61M 2205/583* (2013.01)

(58) Field of Classification Search
CPC .............. A61M 1/1631; A61M 1/1647; A61M 1/3639; A61M 1/3655; A61M 1/3656; A61M 1/3661; A61M 1/3663; A61M 2205/18; A61M 2205/3317; A61M 2205/3327; A61M 2205/3334; A61M 2205/3365; A61M 2205/3368; A61M 2205/52; A61M 2205/581; A61M 2205/582; A61M 2205/583; A61M 2205/70; A61M 2205/702; A61M 2209/02; G01M 3/28; G01M 3/26; F16K 37/0041; F16K 37/0075; F16K 37/0083; F16K 37/0091; F16K 37/00

USPC ....................................................... 604/6.06
See application file for complete search history.

(56) References Cited

U.S. PATENT DOCUMENTS

| | | | |
|---|---|---|---|
| 2009/0292236 A1 | 11/2009 | Kleinekofort | |
| 2012/0330214 A1* | 12/2012 | Peters | A61M 1/1603 604/6.11 |
| 2016/0010755 A1 | 1/2016 | Maenz et al. | |
| 2017/0312411 A1 | 11/2017 | Maierhofer | |
| 2017/0364649 A1 | 12/2017 | Bene et al. | |
| 2018/0318492 A1 | 11/2018 | Peters et al. | |
| 2018/0361051 A1 | 12/2018 | Kopperschmidt | |

FOREIGN PATENT DOCUMENTS

| | | |
|---|---|---|
| DE | 102014100260 A1 | 7/2015 |
| DE | 102014109639 A1 | 1/2016 |
| DE | 102014015048 A1 | 4/2016 |
| DE | 102014015795 A1 | 4/2016 |
| DE | 102015016271 A1 | 6/2017 |
| WO | 2007006348 A1 | 1/2007 |

OTHER PUBLICATIONS

Extended European Search Report for European Application No. 19 154 012.9, dated Jul. 10, 2019, with translation, 15 pages.

* cited by examiner

MONITORING DEVICE AND METHOD FOR MONITORING AN EXTRACORPOREAL BLOOD TREATMENT DEVICE

RELATED APPLICATION

This application claims the benefit of priority of German Application No. 10 2018 102 171.2, filed Jan. 31, 2018, the content of which is incorporated by reference herein in its entirety.

FIELD

The present disclosure relates to a monitoring device for monitoring an extracorporeal blood treatment device, such as a dialysis machine, comprising an extracorporeal blood circuit which has an arterial blood line including an arterial patient port and/or at least one venous blood line including a venous patient port, and a dialysis fluid system which comprises a dialysis fluid supply line and a dialysis fluid drain line. In addition, the present disclosure relates to a method for monitoring an extracorporeal blood treatment device.

BACKGROUND

With external blood treatment devices, such as a dialysis machine, it is important to be able to guarantee perfect treatment of the patient. In particular, fluid flows must be monitored and precisely controlled. Valves are usually used to switch fluid flows or flow paths, be it blood or dialysis fluid, for example. These valves can be, for example, hose pinch valves/hose clamps or also valves directly installed in a line. In this context, it may happen that a valve does not close or open correctly and in particular does not close completely. Reasons for this can be for example particles, calcification or wear, which can obstruct a mechanical closing of the valve or also affect a pump. Especially for valves, which are essential for a correct balancing of the fluid flow, a balancing deviation (ultrafiltration deviation) can occur. If a valve does not close correctly during treatment, this can jeopardize the treatment and entail far-reaching risks for the patient to be treated, in the worst case even lethal consequences.

In dialysis therapy with a dialysis machine, for example, it is common nowadays to perform a so-called self-test of the dialysis machine before each dialysis therapy. This self-test can be used to prove, among other things, that the valves close safely and correctly and can be operated. According to the current state of the art, these self-tests are repeated periodically, for example every one to two hours, in order to carry out a check at discreet intervals. Here, the therapy is interrupted briefly, usually for a few minutes, and then continued. This self-test can therefore detect an internal defect in the dialysis machine. However, the disadvantage is that the periodic self-tests can only be carried out in limited numbers and at intervals. Between the self-tests there remains a time span in which no checking takes place and in which, statistically speaking, no defect is likely to occur. This means that the therapy and the correct functioning of the blood treatment machine cannot be monitored during this time span. In addition, the self-tests interrupt a therapy and prolong both the therapy and the dialysis time.

In addition to the self-tests, fluid or moisture sensors are also used in blood treatment devices to detect a possible leakage. DE 10 2014 100 260 A1, for example, discloses a system in which the humidity of air flowing into the housing is compared with the humidity of air flowing out of the housing. However, the disadvantage here is that the system or the liquid sensors can only detect leaks in an open environment in the housing. If the leakage of the fluid takes place in a closed volume within the housing, the humidity does not change and the defect cannot be detected. Nor is there the possibility for such a system to detect an internal leakage occurring in a circuit (as a special case of the closed volume), in which, for example, a valve does not close correctly.

Apart from this, it is possible to monitor an electrical current or voltage applied to a valve in order to analyze whether the valve is switching properly. Such monitoring is, however, limited to identifying only an electrical fault and cannot assess whether the leakage is due to mechanical blocking or wear of the valve, for example.

Other defects that can occur in a blood treatment machine and especially in a dialysis machine are, for example, a worn pump, maladjusted throttles, clogged filters or wear as well as product defects of technical components.

DE 10 2009 024 864 A1 discloses a method and a device for monitoring a fluid system of an extracorporeal blood treatment device. The pressure is measured in an aeration line branching off from a venous drip chamber and is evaluated, wherein a valve is at least partially opened and closed alternately. The measured pressure signal is therefore subject to pressure fluctuations if there is no fault. A pressure is measured in a supply line and a trigger is used to generate a pressure pulse in addition to the blood treatment device. In addition, it is difficult to open and close a valve cyclically on a dialysis fluid side in order to generate a pressure change as a trigger signal. A valve that does not close correctly can hardly be detected.

WO 2007/006348 A1 and DE 10 2009 060 668 A1 disclose a drug delivery system for liquid drugs and a monitoring device that monitors a flow rate of pumped blood. The use of centrifugal pumps is necessary with the latter document, which limits the design of a dialysis machine. These systems are also difficult to transfer to the dialysis fluid side to determine if there is a defect.

SUMMARY

The objects and aims of the present disclosure are to eliminate or at least reduce the disadvantages of the prior art and in particular to provide a monitoring device and a method which are capable of detecting defects with minimal additional effort at most diverse points of the blood treatment device with great significance and guarantee a safe, reliable, cost-effective and simple monitoring of an extracorporeal blood treatment device as well as shorten the time required for dialysis therapy and also permit fine adjustment of monitoring parameters. In addition, a continuous monitoring during treatment should be possible.

The objects and aims with regard to a generic monitoring device are achieved according to the present disclosure. Thus, the present disclosure is based on the knowledge that the blood treatment device, without further necessary changes to the blood treatment device, continuously provides a sufficient number of measured values/parameters anyway, which have sufficient informative value about the functional reliability of the blood treatment device as a whole or of selected components or sections thereof.

Accordingly, the monitoring device is configured/adapted according to the present disclosure to select and sense/pick up (at least) one measured value/measuring signal/condition-related measured value/parameter occurring during the operation of the extracorporeal blood treatment device and detected/recorded by the extracorporeal blood treatment device, which is suitable for monitoring the blood treatment device with sufficient informative value, to compare a time-related actual course of the detected measured value with a target course/standard course of the associated measured value stored in a memory of the monitoring device and to determine that there is a defect if, at least in sections, the actual course of the detected measured value deviates from the target course of the stored measured value by more than a defined tolerance. In other words, the monitoring device is connected to or can be coupled to at least one sensor/detector of the blood treatment device which detects measured values/status parameters of the extracorporeal blood treatment device.

The monitoring device is accordingly adapted to sense a measured value of the extracorporeal blood treatment device, which for the operation of the extracorporeal blood treatment device is detected with at least one sensor of the blood treatment device. No additional components, such as a trigger for the generation of periodic pressure pulses, are required, but already existing measured values are used which are recorded during the operation of the blood treatment device or during the treatment. In particular, only "core measured values" are used. In this case, "core measured values" means that these measured values must be gathered by the blood treatment device anyway to ensure proper treatment. Thus, as far as possible, an already existing "data pool" of the blood treatment device and existing sensors are used and a malfunction or defect of the device or of one or more selected components of the device is detected by appropriate algorithms and evaluation methods. The fact that different target courses are stored for several different measured values increases the significance of the monitoring device. Correlations between the measured values can also be taken into account. The monitoring device can detect defects at most diverse points of the blood treatment device by evaluating "core measured values". Due to a quasi continuous detection of the measured values throughout the duration of the treatment, it is also possible to deduce that a valve is switching with a delay. If, for example, a valve does not close correctly, the pressure courses change in a characteristic way. This can be determined in particular for valves which are opened and closed cyclically. The monitoring device or the memory of the monitoring device may also preferably have pattern recognition methods stored therein for comparison and determination.

Accordingly, the monitoring device can use detected measured values, such as pressure, temperature, flow rate, conductivity and/or membrane position, to deduce one or more defects during an ongoing treatment or during operation of the blood treatment device without interrupting the treatment, if the comparison of the actual course with the target course shows a deviation exceeding the defined tolerance. By storing a target course in the memory of the monitoring device, a defined (ideal) target can be stored which ensures that the treatment is carried out correctly. With the help of the monitoring device, a defect in the blood treatment device can be implied continuously, safely and reliably and, in particular, internal leaks can be identified efficiently. The target courses can, for example, be defined by experimental measurements in advance or by a computer-aided simulated course.

DE 10 2014 109 639 A1 discloses an example of a dialysis apparatus/dialysis machine which can be monitored with a monitoring device according to the present disclosure. The subject matter of this publication and its functions are hereby fully included in the description as a preferred embodiment of the blood treatment device.

Advantageous embodiments will be explained below.

In a preferred variant, the monitoring device can detect the measured values during operation of the extracorporeal blood treatment device in real time without any time delay, which means that only a physically occurring signal propagation time with associated signal processing occurs, but no further (desired and avoidable) delay. This can create a kind of "online" or real-time monitoring device which enables a user or operator to intervene immediately in the event of a defect determined by the monitoring device or a malfunction of the blood treatment device or a component and enables the monitoring device to detect the defect immediately, i.e. without delay, and to initiate necessary measures, such as an interruption of treatment, for example by closing a valve, or other adequate measures, so that a risk to the patient is excluded or at least minimized. The monitoring device is therefore able to determine a defect or a malfunction of a component of the blood treatment device and thus of the blood treatment device "online", i.e. during the treatment, without interrupting therapy and without additional tests, such as a self-test which is only suitable for determining certain defects. Here, "online" means a method which can be carried out during therapy without interrupting the therapy and without having to carry out dedicated procedures which are only necessary for the detection of a fault. This means that an "online" method allows the detection of a defect solely on the basis of the signal courses caused by the therapy. The term "defect" also refers to a malfunction.

In particular, the monitoring device has an interface with which the monitoring device is connected or can be connected to the extracorporeal blood treatment device, at least in terms of data communication. In particular, this interface can be of the wireless type in the form of Bluetooth® or WLAN, for example. In the event that the monitoring device determines that there is a defect in the blood treatment device, the monitoring device can send a corresponding control command and/or error code via the interface to the blood treatment device so that the latter can initiate adequate measures to protect the patient.

In accordance with a further aspect of the present disclosure, one or more error courses of the measured value may be stored in the memory of the monitoring device (in addition to or possibly as an alternative to the target course of the measured value), wherein the monitoring device determines that there is a defect if the actual course of the detected measured value within a defined tolerance matches the stored error course of the measured value at least in sections. In particular, characteristic error courses of, for example, an incorrectly closing valve, a worn pump with reduced pump performance, a misadjusted throttle with corresponding consequences or a clogged filter can be stored in the memory as a reference. These error courses can be determined experimentally or theoretically in advance. As a result, if only one fault or a limited number of faults occur, a comparison of the actual course with the corresponding error course can also directly imply the cause of error, such as a bent hose or a blockage, so that traceability and repair are facilitated. In particular, the monitoring device can instruct the blood treatment device to perform a detailed self-test and analyze the defect after its determination.

In a preferred embodiment, the monitoring device is able to sense, as a measured value, a voltage and/or current and/or speed of a pump arranged in the extracorporeal blood treatment device in the extracorporeal blood circuit for delivering blood and/or in the dialysis fluid system for delivering dialysis fluid. Here, it can be determined whether there is a defect, since it can be determined via the pump speed, for example, if a downstream or an upstream valve is correctly (completely) closed or whether, contrary to the switching state, a flow is nevertheless permitted. In addition or alternatively, the monitoring device can sense a pressure and/or a temperature and/or a flow and/or a conductivity and/or a membrane position as a detected measured value.

In a preferred embodiment, the monitoring device can detect the actual course of the measured value or of the respective measured values after a start signal for a predetermined detection time and set this detected actual course in each case as the target course of the corresponding measured value stored in the memory of the monitoring device. In this way, for each extracorporeal blood treatment device, an actual course can be recorded individually for each relevant measured value (a kind of checked, correct course), for example after checking that the blood treatment device does function properly, which is then stored in the memory as the target course of the corresponding measured value. The monitoring device can be connected/coupled to different blood treatment devices and calibrated accordingly via the recording. A detailed template and definition of a target course for each relevant measured value already during production of the blood treatment device (for each individual device, with fine calibration) is not necessary. After checking the correct functioning of the blood treatment machine, the target course can also be detected in real time, so that external influences, which occur naturally in the course of production and operation, on a change in the detected measured values can be greatly reduced.

Preferably, a gradient and/or an absolute deviation of the measured value and/or a standard deviation between the actual course and the target course and/or between the actual course and the error course of the measured value can be used as criteria for the defined tolerance. In reality, a theoretically or experimentally determined target course or error course is not hit to 100% by the actual course, but rather the actual course will move within a range, or rather seen descriptively, within a certain tube/corridor as a confidence zone around the target course or error course. If the actual course is within the confidence zone around the target course, the monitoring device decides that there is no defect. If the actual course leaves the confidence zone of the target course, the monitoring device decides that there is a defect. The definition or design of this confidence zone or the defined limits is achieved by the above criteria. In particular, all three criteria, namely a gradient, an absolute deviation of the measured value or a standard deviation, may also be required, so that the monitoring device decides that a defect is present even if there is a deviation from only one criterion. It may also be required that only when the gradient and the absolute deviation of the measured value and the standard deviation of the actual course deviate from the target course or the error course, it is determined that there is a defect. This prevents a false alarm, since all three criteria must be fulfilled. Preferably, an approximation error or a measured value deviation can be used alternatively or additionally.

In addition or alternatively, in a preferred variant, a minimum and/or a maximum over a defined time span of the actual course of the detected measured value compared to the stored target course and/or the stored error course of the measured value can be used as a criterion for the defined tolerance. Here, a kind of limitation of the target course, in which the actual course is to move, can be defined for (time) sections in a kind of step form extending upwards and/or downwards. This time span may be, for example, a balance chamber cycle or a flushing cycle. Preferably, an (absolute) difference between the first and last detected measured values within a defined period can also be used as a criterion.

In a preferred embodiment, the monitoring device can detect and sense at least two (i.e. several) measured values. The monitoring device can use a behavior and/or a correlation of the measured values in relation to each other when comparing the courses and determining that there is a defect. The monitoring device can therefore not only look at the measured values individually and separately from each other, but can also take into account a correlation of the measured values when evaluating the at least two measured values and use this correlation to evaluate or determine whether a defect is present. For example, a pressure and a temperature can be detected. If the pressure and the temperature as well have corresponding courses that correlate with each other, the monitoring device can determine that there is a defect.

According to another aspect of the present disclosure, when a defect is detected and determined by the monitoring device, an acoustic, visual and/or tactile (alarm) signal can be given by an output unit. The malfunction can thus be communicated acoustically, visually and tactilely to an operator of the blood treatment device and, in the event of a malfunction, an intervention can be made in the control of the blood treatment device. For example, the alarm signal could inform the user and the patient, and the user could stop a blood pump and close a venous hose clamp, or if this has already happened automatically, be informed that there is a defect.

The object and the aims of the present disclosure regarding a generic method for monitoring an extracorporeal blood treatment device, such as a dialysis machine, comprising an extracorporeal blood circuit which has an arterial blood line including an arterial patient port and/or at least one venous blood line including a venous patient port, and a dialysis fluid system which comprises a dialysis fluid supply line and a dialysis fluid drain line, wherein during operation of the extracorporeal blood treatment device a detected measured value is sensed, are achieved according to the present disclosure by the following steps: selecting the measured value which is suitable for monitoring the blood treatment device and/or a component of the blood treatment device; continuously sensing and hence detecting the measured value and forming an actual course of this measured value; comparing the actual course of the detected measured value with a target course and/or an error course of the associated measured value; and determining that there is a defect if, at least in sections, the actual course of the detected measured value deviates from the target course by more than a defined tolerance and/or if the actual course of the detected measured value corresponds to the error course within a defined tolerance or matches it. Similar to the monitoring device, the method compares the actual course of the sensed, acquired measured value with the associated target course and/or the error course of the measured value and determines accordingly whether there is a defect. As with the monitoring device, the present disclosure with regard to the method is based on the knowledge that the blood treatment device, without any further necessary changes, already provides sufficient measured values/parameters on a continuous basis which have sufficient significance about the functional reliability of the blood treatment device as a whole or of selected components or sections.

In a preferred embodiment/variant of the method, the comparison step may include the following steps: Forming the standard deviation between the actual course of the measured value and the target course and/or the error course of the measured value; and comparing the value of the formed standard deviation with a stored target standard deviation. The criterion of a standard deviation or sample deviation for the tolerance is a good choice for a function to be implemented, because the standard deviation allows a certain error tolerance over time and a single value, namely the target standard deviation, is sufficient to determine whether the courses correspond to each other. Here, an associated target standard deviation can be defined for the entire time of a treatment or for specific (time) segments.

BRIEF DESCRIPTION OF THE DRAWING FIGURES

The present disclosure is explained in more detail below on the basis of preferred exemplary embodiments with the help of Figures wherein.

The Figures are schematic in nature and only serve to understand the present disclosure. Identical elements are provided with the same reference symbols. The characteristics of the different exemplary embodiments can be exchanged with each other.

DETAILED DESCRIPTION

Figure 1:
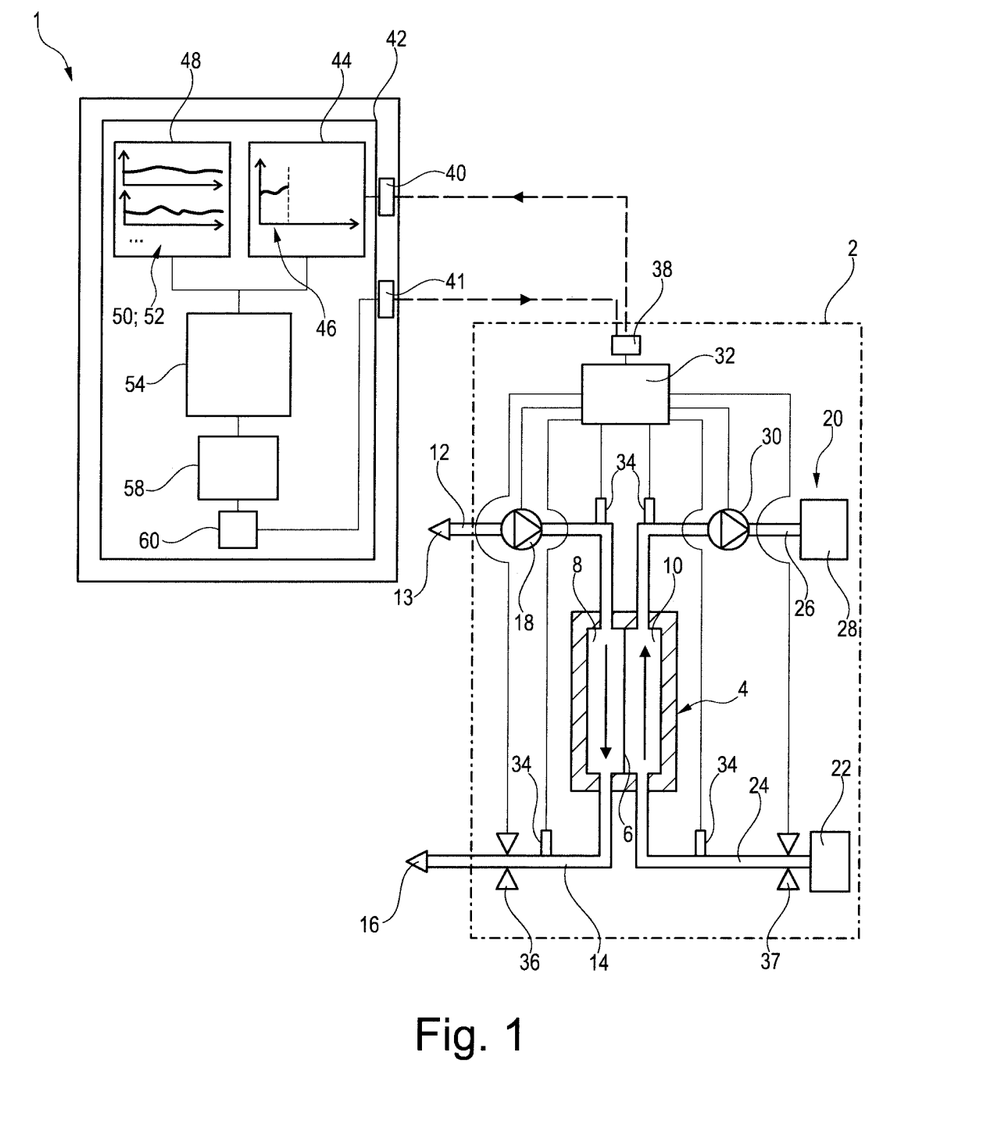
FIG. 1 shows in a very simplified schematic view a first embodiment of a monitoring device with an extracorporeal blood treatment device.

FIG. 1 shows a preferred embodiment of a monitoring device 1 according to the present disclosure. The monitoring device 1 serves to monitor an extracorporeal blood treatment device, in particular a hemo(dia)filtration device, in the manner of a dialysis machine 2 for blood purification or filtration of blood. FIG. 1 shows only the essential components of the blood treatment device in schematic form. The dialysis machine 2 has a dialyzer 4 or filter, which is subdivided by a semi-permeable membrane 6 into a first chamber (blood chamber) 8 and a second chamber (dialysis fluid chamber) 10.

An arterial blood line 12 in the form of a flexible, elastic hose leads from a patient (not shown) from an arterial puncture cannula 13 (as an arterial patient port) to the first chamber 8 of the dialyzer 4. The direction of flow of the blood is indicated by an arrow in FIG. 1. A venous blood line 14 returns to the patient from the outlet of the first chamber 8. The venous blood line 14 in the form of a flexible, elastic hose is connected to the patient with a venous puncture cannula 16 on a shunt or fistula. A peristaltic blood pump 18 is arranged in the arterial blood line 12 to convey the patient's blood. In addition, a bubble trap (not shown) is arranged in the venous blood chamber to remove air from the pumped blood before recirculation.

A dialysis fluid system 20 of the blood treatment device comprises a dialysis fluid source 22 to which a dialysis fluid supply line 24 is connected which leads into the second chamber 10 of the dialyzer 4. From the outlet of the second chamber 10, a dialysis fluid drain line 26 branches off and leads to a dialysis fluid outflow 28. The dialysis fluid is conveyed in the dialysis fluid system 20 by at least one dialysis fluid pump 30, such as a peristaltic pump or a centrifugal pump.

The dialysis machine 2 is controlled by an electronic control unit (ECU) 32. The ECU 32 controls, among other things, the blood pump 18 and the dialysis fluid pump 30, and on the other hand the ECU 32 detects measured values from the blood treatment device. To this end, a sensor 34 is attached to each of the lines, namely the arterial blood line 12, the venous blood line 14 as well as the dialysis fluid supply line 24 and the dialysis fluid drain line 26. The sensor 34 in this embodiment is always the same sensor 34 and detects a pressure, a temperature and a flow rate of the respective line 12, 14, 24, 26. It goes without saying that different sensors with different modes of operation, depending on the application, can be arranged instead. Of course, for example, only one sensor 34 could be arranged on the venous blood line 14, which only measures the pressure as a measured value. The only important thing is that the dialysis machine 2 has at least one sensor 34 to detect measured values for the ECU 32.

The sensors 34 forward the data/information of the measurement signals or measured values to the ECU 32 either wired or wirelessly. To actuate or control the blood-side circulation, the dialysis machine 2 features, among other things, a valve in the form of an electromagnetic hose clamp 36, which seals off the hose of the venous blood line 14 in a squeezing manner and thus stops the blood flow. When the venous hose clamp is closed, the fluid flow in the extracorporeal blood circulation is interrupted. On the side of the dialysis fluid system 20, the dialysis machine 2 also has a valve 37, which can control and stop the flow through the dialysis fluid supply line 24. The dialysis machine 2 also has an interface 38 via which the dialysis machine 2 is connected to the monitoring device 1 in tenns of data transfer. For the sake of understanding and illustration, the data flow of the connection is separated in data output and data input in FIG. 1. If, for example, the valve 37 does not close correctly, the monitoring device 1 can detect this.

The extracorporeal blood treatment device 2 is also provided with balance chambers for volumetric balancing of liquids. A balance chamber is a chamber that is divided into two compartments by an elastic membrane. Depending on how much liquid is present in each of the two compartments, the membrane is deflected either to the one or the other compartment. Using a position sensor, the extracorporeal blood treatment device 2 can measure the position of the membrane. In addition, conductivity cells are provided in the extracorporeal blood treatment device 2 to add dialysis concentrates in the correct concentration to a dialysis fluid. During operation of the extracorporeal blood treatment device 2, the corresponding signal courses of the conductivities are detected.

The dialysis machine 2 transmits the data of the measured values detected, e.g. of pressure, temperature and flow rate of all four lines, via the interface 38 in real time, i.e. without delay, to a receiving unit 40 (as part of an interface on the side of the monitoring device) of the monitoring device 1, which means that only a physically occurring signal propagation time with associated signal processing occurs, but no further (desired and avoidable) delay, which may be done wirelessly and alternatively or in addition also in wired fashion. The receiving unit 40 forwards the detected and sensed measured values to a central control unit 42, which selects and processes the measured values. The central control unit 42 has an acquisition memory 44 in which an actual course 46 is detected, as well as a memory 48 in which target courses 50 of the respective measured values are stored. In addition to the target courses 50 of the respective measured values, error courses 52 for the corresponding measured values are also stored in memory 48. The acquisition memory 44 as well as the memory 48 may also be physically formed in a combined, single memory element.

A comparison unit 54 of the monitoring device 1 compares for each measured value the actual course 46 with the target course 50 and the actual course 46 with the error course(s) 52. If the actual course 46 deviates from the target course 50 by more than a defined tolerance 56, a determination unit 58 determines that there is a defect in the dialysis machine 2. In other words, the determination unit 58 determines whether there is a defect on the basis of the result of the comparison carried out by the comparison unit 54. This is the case if the actual course 46 deviates from the target course 50 by more than a defined tolerance 56. The determination unit 58 also determines that a defect exists if the actual course 46 within a defined tolerance 56 corresponds to or coincides with an error course 52. The comparison of the respective actual course with the corresponding target or error courses by the comparison unit 54 and the execution of the determination by the determination unit 58 as to whether there is a defect are explained in detail in the description of FIGS. 2 and 3.

If it is determined that there is a defect, an acoustic, a visual and/or a tactile alarm signal is issued via an output unit in the form of an alerting unit 60. A control command is also sent by the alerting unit 60 via a transmitting unit 41 to the interface 38 of the dialysis machine 2. As an alternative or in addition to the control command, it is also possible that the monitoring device 1 only sends an error code to the ECU 32 of the dialysis machine 2 via the transmitting unit 41. The dialysis machine 2 can then use the error code to determine independently which measures are to be taken in accordance with the error code. Thus, the dialysis machine 2 continues to operate "autonomously" and the control power is solely on the part of the dialysis machine 2. The control command can preferably give the instruction to the ECU 32 of the dialysis machine 2 to stop the blood pump 18 and the dialysis fluid pump 30 as well as to completely close the electromagnetic hose clamp 36 and the valve 37. Also, if, for example, the valve 37 does not close completely, although it should be closed for e.g. a dialysis fluid change, it can be determined by means of the sensors 34 and finally the monitoring device that there is a defect. After this, the hose clamp 36 is closed immediately. This measure allows to directly and immediately prevent the patient from being endangered if a defect has been detected.

Figure 2:
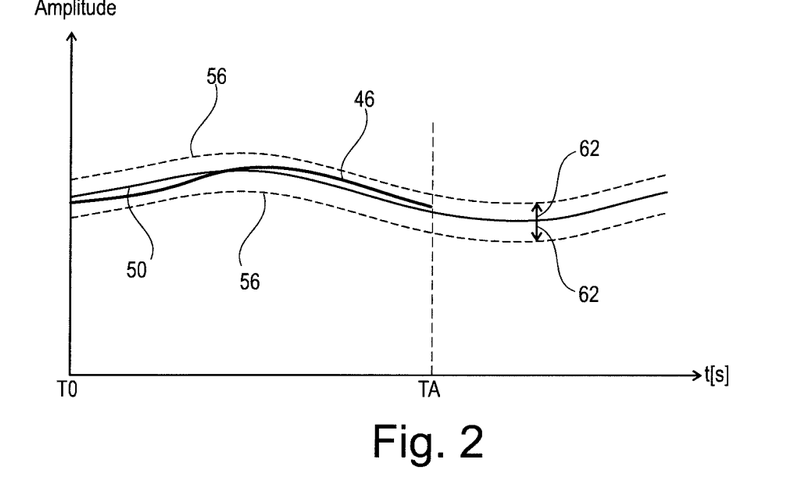
FIG. 2 shows a graph of a comparison of the monitoring device, in which an actual course within a tolerance is compared with a target course.

FIG. 2 clearly shows a graph with exemplary courses to explain the exact function of the comparison and determination by the comparison unit 54 and the determination unit 58, respectively. The abscissa axis represents the time (for the course), and the ordinate axis shows an amplitude or an absolute value of the measured value of the courses. Stored in the memory 48 of the monitoring device 1 is the target course 50 in the form of a sinusoidal curve (for the sake of illustration). The criterion selected for the tolerance 56 is an absolute measured value deviation with a constant deviation value 62, which applies both in the negative and the positive direction (of the amplitude). This results in a kind of corridor/tube/margin around the target course 50 as a defined tolerance 56 or confidence zone.

The actual course 46 is also plotted in FIG. 2. The actual course 46 is recorded starting at a point in time T0 (the start of the recording of the measured values or the start of treatment, for example) and is detected until a current time TA and stored in the acquisition memory 44. As can be seen from FIG. 2, the actual course 46 lies within the tolerance 56 of the target course 50 for the corresponding measured value. Thus, the monitoring device 1 does not decide that there is a defect, or in other words, the monitoring device 1 determines that there is currently no defect.

At this point it should be noted that the graph shown in FIG. 2 is valid for exactly one measured value (of one line, of course). For example, an actual course 46 of the pressure of the venous blood line 14 is shown in FIG. 2. In the same way, of course, a measured value such as a temperature of the dialysis fluid supply line 24 can also be used.

Figure 3:
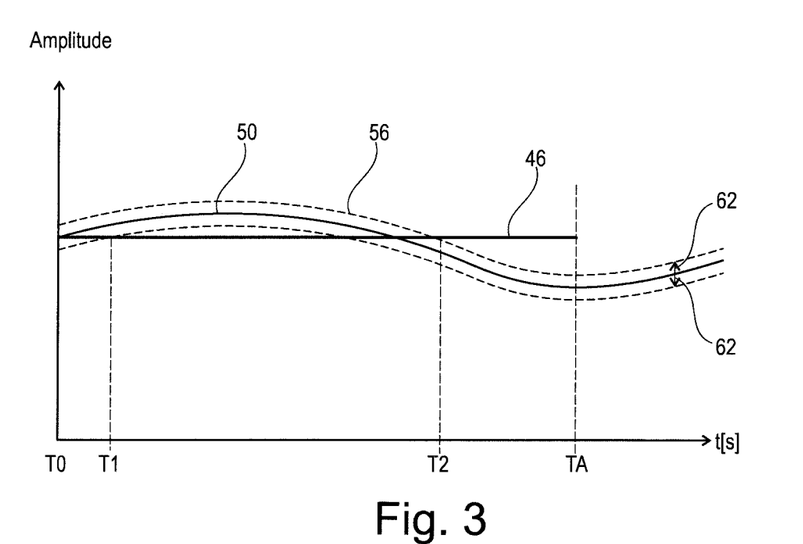
FIG. 3 shows a graph of a comparison of the monitoring device, in which the actual course does not correspond to the target course.

FIG. 3 shows an actual course 46, in which the actual course 46 is constant but also extends partially outside the tolerance 56 of the target course 50. The monitoring device 1 determines at a first point in time T1, at which the actual course 46 leaves the tolerance 56, or, if a certain time for the actual course 46 lying outside the tolerance 56 would be granted, at the latest at a second point in time T2, that there is a defect in the dialysis machine 2. The treatment is stopped, the pumps 18, 30 are halted and the hose clamp 36 is closed.

Figure 4:
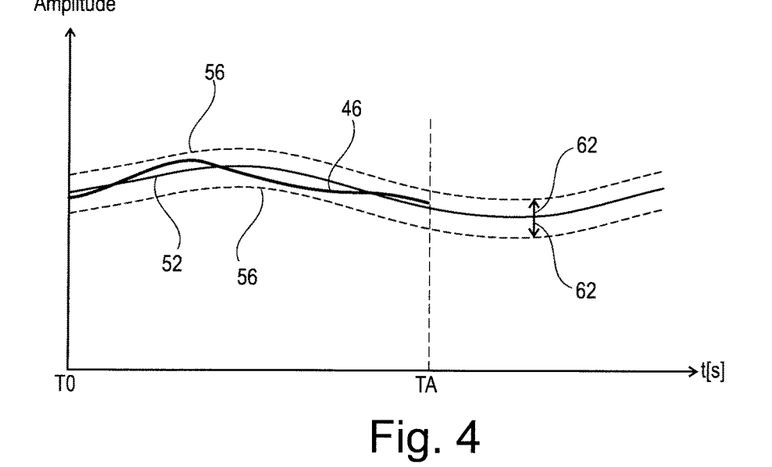
FIG. 4 shows a graph of a comparison of the monitoring device, in which an actual course within a tolerance is compared with an error course.

FIG. 4 shows, similar to the comparison from FIG. 2, a comparison of the actual course 46 with the error course 52. The monitoring device 1 compares not only the target course 50 but also the error course 52 with the same procedure, but with the difference that, if the actual course 46 lies within the tolerance 56 of the error course 52, the determination unit 58 or the monitoring device 1 now determines that there is actually a defect.

Figure 5:
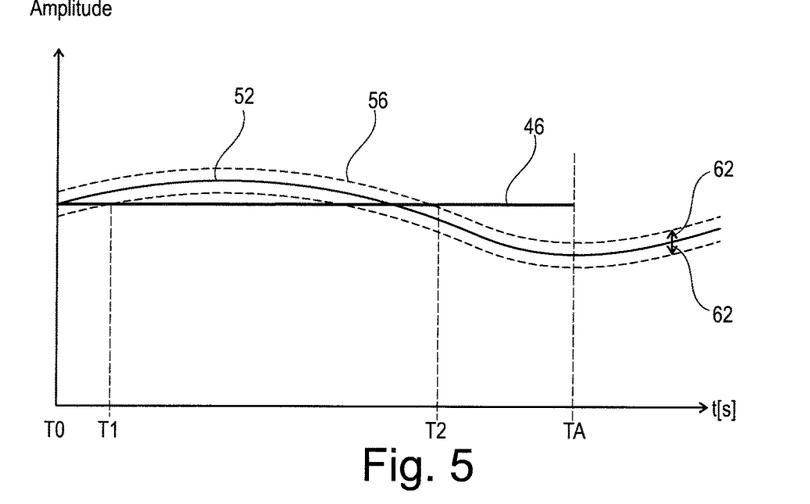
FIG. 5 shows a graph of a comparison of the monitoring device, in which the actual course does not correspond to the error course.

Similar to the comparison in FIG. 3, FIG. 5 shows a comparison of the actual course 46 with the error course 52, in which the actual course 46 does not follow the error course 52. It is determined that (with the exception of the areas around the points in time T1 and T2) the actual course 46 does not correspond to the error course 52 and therefore there is no defect. The transits of the actual course 46 into the area of the corridor/tube (tolerance 56) around the error course 52 must of course be evaluated and it must be defined that these deviations lie outside the tolerance.

It is important that for each single, individual measured value, such as the temperature, a separate target course 50 or one or more error courses 52 for exactly this measured value for exactly this line are stored in the memory 48. If necessary, it is even possible to store several target courses for each individual measured value, for example for different types of therapy or modes of the extracorporeal blood treatment device.

Figure 6:
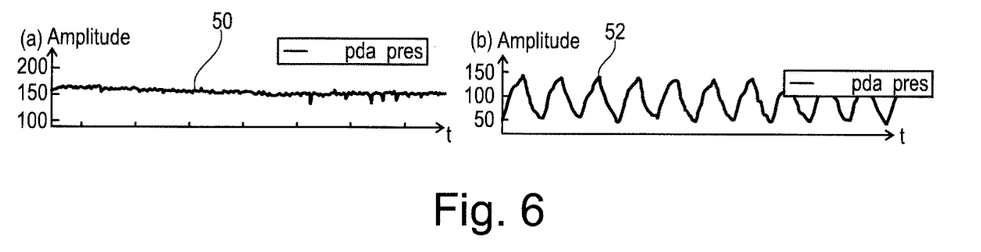
FIG. 6 shows a graph with an exemplary comparison of a target course and an error course.

FIG. 6 is a graph where the left part of FIG. 6 shows an exemplary pressure course (PDA—pressure sensor dialysis fluid outlet) for a normal therapy according to a target course 50 for illustration, whereas the right part of FIG. 6 shows a pressure course according to an error course 52 as a measured value, in which a defect is present and a therapy of the patient is disturbed. The error course 52 represents a therapy with a defective balance chamber valve, where the balance chamber valve does not close correctly. As a result, the graph or pressure course occurs in the form of a sawtooth profile.

Figure 7:
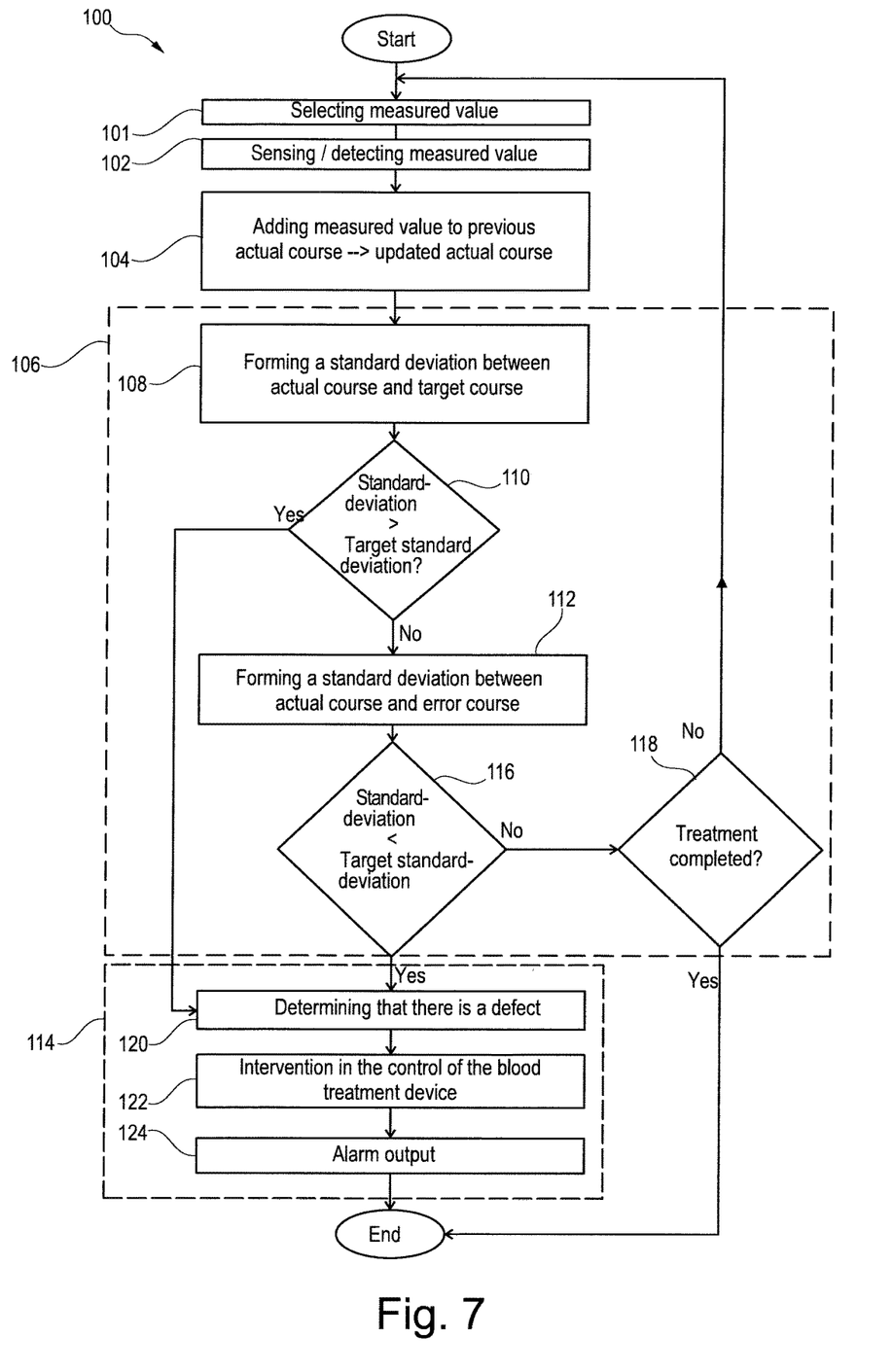
FIG. 7 shows a flowchart of a method of the present disclosure for monitoring an extracorporeal blood treatment device according to a preferred embodiment.

FIG. 7 shows a method 100 according to the present disclosure of a preferred embodiment/variant for monitoring an extracorporeal blood treatment device, such as a dialysis machine 2 (see FIG. 1), comprising an extracorporeal blood circuit which has an arterial blood line 12 including an arterial patient port 13 and/or at least one venous blood line 14 including a venous patient port 16, and a dialysis fluid system 20, wherein during the operation of the extracorporeal blood treatment device a measured value acquired is sensed by the monitoring device. After the start of the method 100, a selection is performed in step 101 and a continuous sensing and hence detection of the measured value is performed in step 102. The method shown is described for one measured value, for example the pressure of the venous blood line 14. Of course, not only one measured value but also several measured values, such as pressure, temperature and flow rate, can be taken from different sections of the lines of the blood treatment device. The method 100 is then performed for each individual measured value.

After the step of sensing 102, the method 100 according to the present disclosure progresses to the step of adding 104 the measured value detected to the previous actual course. This adds the current value of the measured value to an actual course detected up to that time, so that the updated actual course is available to the method 100 continuously and up to date. After the step of adding 104, the following block of comparison 106 compares the actual course with a target course and with an error course. Specifically, the procedure proceeds to a step 108 of forming a standard deviation target course, where a standard deviation is formed between the actual course and the target course. In particular, in this step a standard deviation of the individual continuously detected measured values from point in time T0 to current time TA (see also FIGS. 2 and 3) is formed. Instead of point in time T0, it is also conceivable to select a later point in time in order to analyze only a certain time span in the past and to form the standard deviation between the actual course and the target course in this time span.

The result of the formation of the standard deviation in step 108 is an absolute value that is compared in condition 110 with a stored target value or a stored target standard deviation. If the value of the standard deviation is less than the target standard deviation (No), and the actual course is therefore within the tolerance of the target course, the method proceeds to a step 112 of forming a standard deviation error course. If it should be the case, however, that the standard deviation calculated in condition 110 is greater than the target standard deviation (Yes), the actual course is outside the tolerance of the target course and the method proceeds to a block 114 of defect determination.

In the step 112 of forming a standard deviation error course, the standard deviation between the actual course and a stored error course is carried out, essentially similar to the step 108 of forming a standard deviation target course. Here, too, any time span T1 or T2 to TA can be used instead of the time span T0 to TA.

A subsequent condition 116 checks whether the calculated standard deviation is less than a target standard deviation. This target standard deviation of condition 116 may differ from the target standard deviation of step 108, depending on the definition. In this embodiment, both target standard deviations should be the same in order to have a variable to be controlled centrally. If the calculated standard deviation is less than the target standard deviation (Yes), the comparison has shown that the actual course lies within the tolerance of the error course. As with condition 110, the method then proceeds to the block 114 of defect determination. However, if the standard deviation is greater than the target standard deviation, the method proceeds to a condition 118 which checks whether the treatment has been completed. At this point it should be noted that of course several error courses 52 can also be stored for exactly one measured value. If this is the case, step 112 and condition 116 are run again for each further existing error profile, so that the method proceeds to the condition 118 or the block 114 defect determination only after all error profiles of the measured value have been checked.

In condition 118, the status of the treatment is checked. If the treatment is not yet completed (No), another loop is added to the method by directing it to the step 102 of sensing. If, on the other hand, the patient's treatment is completed (No), there is no need to monitor the blood treatment device and the method ends.

The block 114 defect determination includes the step 120 of determining a defect, the step 122 of intervening in the control of the blood treatment device 122 and the step 124 of alerting. In the step 122 of intervening in the control of the blood treatment device 122, the blood treatment device is stopped, the pumps are halted and, in particular, a valve or hose clamp of the venous blood line and a valve of the dialysis fluid supply line 24 are closed by the method, for example via a sent control command and/or a corresponding error code going to the blood treatment device. The step 124 of alerting may be realized by an optical alarm output, for example on a display of the blood treatment device, a flashing light, an acoustic alarm output in the form of a beep and a tactile alarm output such as a vibration. After the block 114 of defect determination, the method according to the present disclosure of this embodiment stops.

The invention claimed is:

1. A monitoring device for monitoring an extracorporeal blood treatment device that comprises an extracorporeal blood circuit which has an arterial blood line with an arterial patient port and/or at least one venous blood line with a venous patient port, and a dialysis fluid system which has a dialysis fluid supply line and a dialysis fluid drain line, the monitoring device configured to select and sense a measured value occurring and detected by and during operation of the extracorporeal blood treatment device which is suitable for monitoring the extracorporeal blood treatment device, to compare a time-related actual course of the measured value with a target course of the measured value stored in a memory of the monitoring device and to determine that there is a defect if the actual course of the measured value deviates from the target course of the measured value by more than a defined tolerance, wherein one or more error courses of the measured value are stored in the memory of the monitoring device in addition to the target course of the measured value, and the monitoring device determines that there is a defect if the actual course of the measured value coincides with one of the one or more error courses of the measured value within a defined tolerance.

2. The monitoring device according to claim 1, wherein the monitoring device detects the measured value during operation of the extracorporeal blood treatment device in real time without any time delay.

3. The monitoring device according to claim 1, wherein the monitoring device senses a voltage, a current and/or a rotational speed of a pump arranged in the extracorporeal blood treatment device in the extracorporeal blood circuit for conveying blood and/or in the dialysis fluid system for conveying dialysis fluid, as the measured value.

4. The monitoring device according to claim 1, wherein the monitoring device senses a pressure, a temperature, a flow, a conductivity and/or a membrane position as the measured value.

5. The monitoring device according to claim 1, wherein the monitoring device detects the actual course of the measured value after a start signal for a predetermined detection time and defines said actual course in each case as the target course of the measured value.

6. The monitoring device according to claim 1, wherein a gradient, an absolute measured value deviation and/or a standard deviation between the actual course and the target course and/or between the actual course and the one or more error courses are used as criterion for the defined tolerance.

7. The monitoring device according to claim 1, wherein a minimum and/or a maximum over a defined time span of the actual course of the measured value with respect to the target course and/or the one or more error courses of the measured value are used as criterion for the defined tolerance.

8. The monitoring device according to claim 1, wherein at least two measured values are detected and sensed, and the monitoring device uses a behavior and/or a correlation of the at least two measured values between them when comparing the actual course and the target course, and determining whether there is a defect.

9. The monitoring device according to claim 1, wherein, when a defect is determined by the monitoring device, an acoustic, visual and/or tactile signal is output by an output unit and/or a corresponding error code is output to the extracorporeal blood treatment device.

10. A method for monitoring an extracorporeal blood treatment device, that comprises an extracorporeal blood circuit which has an arterial blood line with an arterial patient port and/or at least one venous blood line with a venous patient port, and a dialysis fluid system comprising a dialysis fluid supply line and a dialysis fluid drain line, wherein during operation of the extracorporeal blood treatment device a detected measured value is sensed, comprising the steps of:
 selecting the measured value which is suitable for monitoring the extracorporeal blood treatment device and/or a component of the extracorporeal blood treatment device;
 continuously sensing and detecting the measured value;
 comparing an actual course of the measured value with one or more error courses of the measured value stored in a memory; and
 determining that there is a defect if the actual course of the measured value coincides with one of the one or more error courses of the measured value within a defined tolerance.

11. The method for monitoring according to claim 10, wherein the step of comparing an actual course of the measured value with one or more error courses of the measured value comprises the following steps:
 calculating a standard deviation between the actual course of the measured value with the one of the one or more error courses of the measured value;
 comparing the standard deviation with a stored target standard deviation.

12. A monitoring device for monitoring an extracorporeal blood treatment device that comprises an extracorporeal blood circuit which has an arterial blood line with an arterial patient port and/or at least one venous blood line with a venous patient port, and a dialysis fluid system which has a dialysis fluid supply line and a dialysis fluid drain line, the monitoring device configured to select and sense a measured value occurring and detected by and during operation of the extracorporeal blood treatment device which is suitable for monitoring the extracorporeal blood treatment device, to compare a time-related actual course of the measured value with one or more error courses of the measured value stored in a memory of the monitoring device and to determine that there is a defect if an actual course of the measured value coincides with one of the one or more error courses of the measured value within a defined tolerance.

* * * * *